United States Patent [19]

Schulte-Elte et al.

[11] Patent Number: 4,626,602
[45] Date of Patent: Dec. 2, 1986

[54] ALIPHATIC ALCOHOLS, THEIR PREPARATION AND USE OF SAME AS PERFUMING INGREDIENTS

[75] Inventors: Karl-Heinrich Schulte-Elte, Onex; Hervé Pamingle, Geneva, both of Switzerland

[73] Assignee: Firmenich SA, Geneva, Switzerland

[21] Appl. No.: 804,249

[22] Filed: Dec. 4, 1985

Related U.S. Application Data

[63] Continuation of Ser. No. 594,192, Mar. 28, 1984.

[30] Foreign Application Priority Data

Apr. 12, 1983 [CH] Switzerland .................. 1963/83
Aug. 30, 1983 [CH] Switzerland .................. 4743/83

[51] Int. Cl.$^4$ .................. C07C 35/08; C11B 9/00
[52] U.S. Cl. .................. 568/822; 568/828; 252/522 R; 585/275
[58] Field of Search .................. 568/822, 828; 252/522 R; 585/275

[56] References Cited

U.S. PATENT DOCUMENTS 4,181,631  1/1980  Shaffer et al. .................. 568/822
4,252,986  2/1981  Klein et al. .................. 568/822

OTHER PUBLICATIONS

Hilgetag and Martini, *Preparative Organic Chemistry*, 4th ed., pp. 32–34, (John Wiley and Sons).
Morrison and Boyd, *Organic Chemistry*, 3rd ed. sections 6.3 and 19.10, (Allyn and Bacon).

*Primary Examiner*—Werren B. Lone
*Attorney, Agent, or Firm*—Pennie & Edmonds

[57] ABSTRACT

Novel cycloaliphatic alcohols of formula

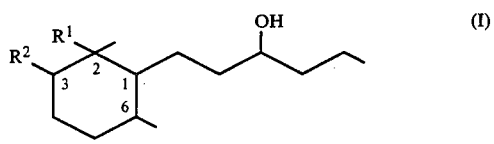

wherein each of symbols $R^1$ and $R^2$ designates a methyl radical or wherein $R^1$ designates an ethyl radical and $R^2$ stands for a methyl radical or a hydrogen atom, possess useful fragrance properties and consequently can be used in the perfume industry.

A process for their preparation starting from an allenic carbinol is disclosed.

14 Claims, No Drawings

ALIPHATIC ALCOHOLS, THEIR PREPARATION AND USE OF SAME AS PERFUMING INGREDIENTS

This is a continuation of application Ser. No. 594,192, filed Mar. 28, 1984.

BRIEF SUMMARY OF THE INVENTION

This invention provides novel cycloaliphatic alcohols of formula

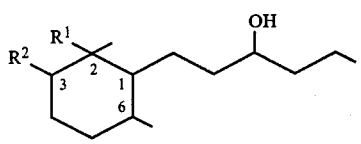

wherein each of symbols $R^1$ and $R^2$ designates a methyl radical or wherein $R^1$ designates an ethyl radical and $R^2$ stands for a methyl radical or a hydrogen atom.

The instant invention provides further a perfume composition containing an odorous effective amount of a compound of said formula (I).

The invention relates also to a method to improve, enhance or modify the fragrance properties of perfumes and perfumed articles which method consists in adding thereto an odorous effective amount of a compound of formula (I).

The invention provides a process for the preparation of the cycloaliphatic alcohols of formula (I), which comprises the step of reducing an allenic carbinol of formula

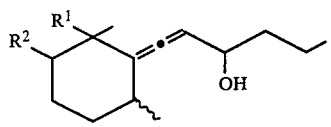

wherein ∼∼∼ stands for a single carbon-carbon bond of cis- or trans-configuration, which reduction is carried out by catalytic hydrogenation in homogeneous or heterogeneous phase, at super-atmospheric pressure and in the presence of a noble metal catalyst.

BACKGROUND OF THE INVENTION

The prior art describes the odorous properties, viz. the fixative characters, of 1-(2,6,6-trimethylcyclohexyl)-hexan-3-ol [see DE-AS No. 28 07 584, which corresponds to U.S. Pat. No. 4,252,986], also known under the name of 10-ethyl-tetrahydroionol. The prior art discloses further certain derivatives of the said compound, which derivatives contain either a branched, hydroxylic side-chain or a "shortened" hydroxylic chain possessing five carbon atoms [Dragoco Report 199 (1980)].

The above cited references, not only are mute as to the interest presented by compounds of formula (I), but also suggest that compounds other than 10-ethyl-tetrahydroionol possess fragrance properties significantly less developed than those shown by it.

It is with surprise therefore that we discovered that "methylated" compounds (I) not only possessed fragrance characteristics of great interest, but also that their properties were in effect superior to those shown by 10-ethyl-tetrahydroionol with respect to both their quality and their strength. We have discovered also unexpectedly that there existed a marked difference between the fragrance qualities of the distinct isomers of this series of compounds. Trans cyclanic isomers were judged far superior to their corresponding cis derivatives.

Whenever mention is made hereinafter to cis or trans cyclanic isomerism, we intend to refer to the particular configuration of the hydroxyhexyl group with respect to the methyl radical in position 6 of the hexanic ring.

One of the object of the present invention reverts to the use as perfuming ingredients of the compounds of formula (I) in their trans configuration or of mixtures containing proportions of more than 50% by weight of said compounds and less than 50% by weight of their corresponding cis isomers.

Furthermore, we could establish also that in the case of compounds (I) having $R^1$=ethyl and/or $R^2$=methyl, the specific isomers having at the same time the different substituents at positions 1, 2 and/or 3 and 6 of the hexanic ring in the equatorial configuration possessed odorous features more pronounced than those of their corresponding stereoisomers of opposite configuration.

Thus, for example, the compound of structure

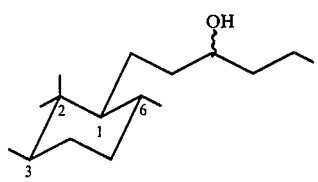

whose substituents in positions 1, 3 and 6 of the hexanic ring have the equatorial position, possesses a powerful odor of steroidal, animal, woody, or even ambery character. This odor character, accompanied by a sweaty note, is also found in the compound of formula

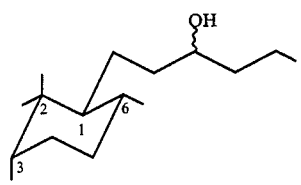

having the methyl radical in position 3 in the axial configuration. Its odor strength however is less pronounced than that of the earlier compound.

Thanks to the present invention, it is now possible to prepare a product essentially consisting of the most olfactively interesting isomers.

PREFERRED EMBODIMENTS OF THE INVENTION

The process of the invention consists in reducing an allenic carbinol of formula

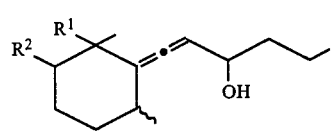

wherein ∼∼∼ stands for a single carbon-carbon bond of cis or trans configuration, by means of a catalytic hydrogenation in homogeneous or heterogeneous phase, at super-atmospheric pressure and in the presence of a noble metal catalyst.

Suitable catalysts include palladium, platinum, optionally on charcoal, and rhodium.

The pressure employed varies in a wide range. Typically, it can be of between about 25 and 150 atmospheres.

The product thus obtained is essentially consisting of the desired trans isomer of formula

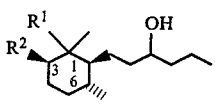
(a)

accompanied by minor amounts of the isomers of formula

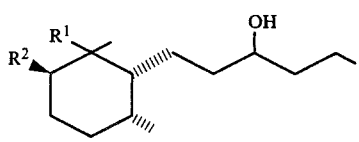
(b)

and of formula

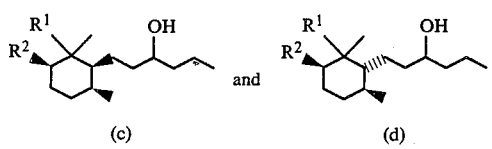

(c)            (d)

The mixture obtained can be further enriched with desired isomer (a) by a separation via gas-chromatography.

Allenic carbinols (II), used as starting materials in the above described process, can be prepared according to a process which can be illustrated by the following reaction pathway:

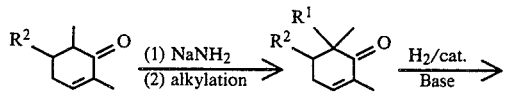

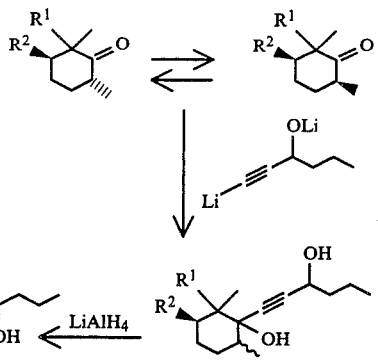

For all practical purposes, the isomeric mixture of allenic carbinols obtained directly by the above described process can be used for the next reaction step.

As indicated above, the process of the invention enables the preparation of compounds (I) eminently in their tri-equatorial configuration visà-vis the substituents in asymmetric centres 1, 3 and 6.

An original process has been also developed for the preparation of the other trans isomers of interest for perfumery, which process comprises the reduction of a ketone of formula

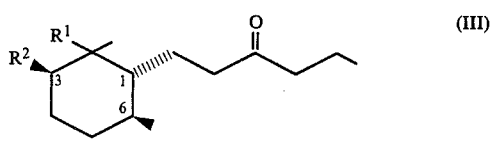
(III)

with an alkali metal alumino-hydride to give the desired carbinol of formula

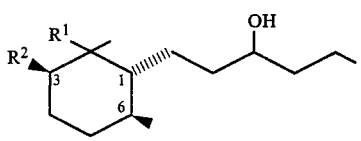

Ketones (III) used as starting materials in the above process can be prepared as follows:

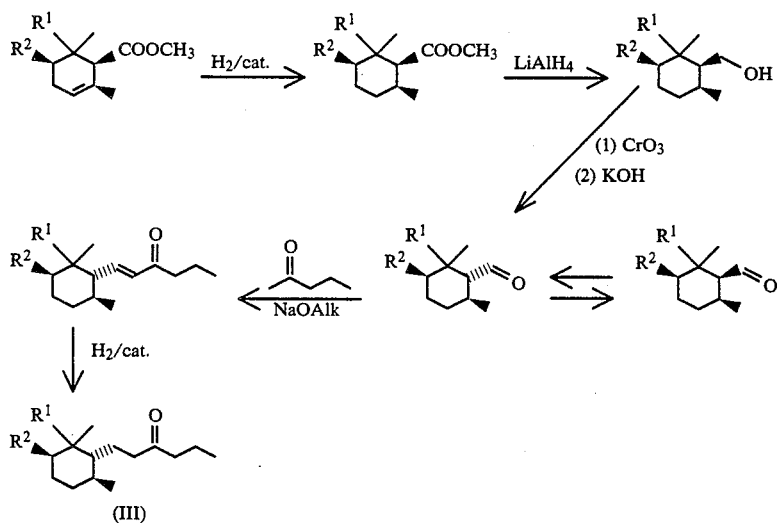

(III)

The processes defined above are described in a detailed manner in the examples which follow.

As will be appreciated by those skilled in the art, the amount of the products of the invention employed in a particular instance can vary over a relatively wide range, depending upon the odorous effect to be achieved. As usual in the art, the perfumer shall determine the best concentrations as a function of the product it is desired to perfume and of the nature of the coingredients he has chosen in a particular blend. The primary requirement is to obtain a well balanced overall olfactive effect of pleasant character. Concentrations of the order of about 1 to 10% by weight of the compounds of the invention based on the total weight of the composition into which it is added, can achieve the desired effect. Of course, concentrations lower than the above given values can be employed to perfume articles such e.g. soaps, cosmetics or detergents.

The active compounds of the invention can be used either in their isolated form or, more frequently, in solution in the current solvents such as ethanol, anozol, diethyl phthalate, or preferably in admixture with other usual perfume coingredients, supports or diluents.

Vis-a-vis the known analog, 1-(2,6,6-trimethylcyclohexyl)-hexan-3-ol [mixture eminently consisting of cis cyclanic isomer; TIMBEROL, trade name of Dragoco, Holzminden FRG] the compounds of the instant invention, viz. the compounds having substituents in positions 1, 2 and/or 3 and 6 of the hexanic ring in equatorial position, possess a more distinct note and a more pronounced ambery and animal character. Their odor strength is also superior to that of TIMBEROL, being estimated at about 20–25 times greater than that of this latter compound.

The invention is illustrated in a more detailed manner by the following examples wherein the temperatures are indicated in degrees centigrade and the abbreviations have the meaning common in the art.

EXAMPLE 1

Preparation of 1-(2,2,3,6-tetramethyl-1-cyclohexyl)-3-hexanol

2 G (8.5 mM) of 1-(2,2,3,6-tetramethyl-1-cyclohexylidene)-1-hexen-3-ol in 20 ml of ethyl acetate were hydrogenated in the presence of 0.2 g of palladium at 5% on charcoal, in an autoclave containing a hydrogen atmosphere maintained at a pressure of 100 atm. After filtration, the mixture was concentrated and distilled by means of a bulb apparatus (bath temp.: about 130°) under reduced pressure. There were thus obtained 1.9 g (yield 95%) of a mixture containing about 80% by weight of 1-(2,2,c-3,t-6-tetramethyl-r-1-cyclohexyl)-3-hexanol and 10% of 1-(2,2,t-3,c-6-tetramethyl-r-1-cyclohexyl)-3-hexanol accompanied by minor amounts of 1-(2,2,c-3,c-6-tetramethyl-r-1-cyclohexyl)-3-hexanol and 1-(2,2,t-3,t-6-tetramethyl-r-1-cyclohexyl)-3-hexanol.

The analytical characteristics of 1-(2,2,c-3-t-6-tetramethyl-r-1-cyclohexyl)-3-hexanol were as follows:

IR: 3350 cm$^{-1}$;

NMR: 0.45 (m, 1H); 0.65 (s, 3H); 0.8–0.95 (m, 12H); 1.0–1.65 (m, 14H); 3.55 (m, 2H) δppm:

MS: M$^+$=240; m/e: 222 (3), 207 (4), 197 (4), 179 (6), 161 (1), 152 (18), 145 (1), 137 (20), 131 (1), 123 (40), 103 (46), 95 (63), 83 (93), 69 (91), 55 (100), 41 (50).

1-(2,2,t-3,c-6-tetramethyl-r-1-cyclohexyl)-3-hexanol

IR: 3350 cm$^{-1}$;

NMR (360 MHz; CDCl$_3$): 0.7 and 0.75 (3H, 2s); 0.82–0.95 (12H); 1.1–1.65 (14H), several m); 1.9 (1H, m); 3.6 (1H, m) δppm;

MS: M$^+$=240; m/e: 222 (7), 207 (16), 197 (4), 179 (8), 166 (5), 152 (18), 137 (28), 123 (35), 109 (39), 95 (46), 83 (57), 69 (66), 55 (100), 42 (71).

1-(2,2,c-3,c-6-tetramethyl-r-1-cyclohexyl)-3-hexanol

IR: 3350 cm$^{-1}$;

NMR (360 MHz; CDCl$_3$): 0.7 and 0.72 (3H, 2s); 0.82–0.9 (9H); 0.95 (3H, t); 1.1–1.7 (14H, several m); 1.9 (1H, m); 3.6 (1H, m) δppm;

MS: M$^+$=240; m/e: 222(9), 207(42), 197(2), 179(8), 166(10), 152(11), 137(50), 123(41), 109(41), 95(51), 83(48), 69(65), 55(100), 41(69).

1-(2,2,3,6-Tetramethyl-1-cyclohexylidene)-1-hexen-3-ol, used as starting material in the above process, can be prepared as follows:

a. 2,5,6,6-Tetramethyl-2-cyclohexen-1-one

This compound was prepared according to the process described in DE-OS No. 24 44 585 with a yield of 95%.

b. 2,2,3,6-Tetramethyl-1-cyclohexanone

152 G (1M) of the ketone obtained according to paragraph a. above were hydrogenated in 500 ml of methanol in the presence of 5 g of palladium at 5% on charcoal. After absorption of about 23 lt of hydrogen, the mixture was filtered, concentrated under reduced pressure and distilled over a Vigreux column to give 123 g of the desired ketone having b.p. 73°–6°/5.32×10$^2$ Pa; yield 80%.

The product thus obtained was then placed under nitrogen in a reaction vessel and refluxed in admixture with 100.8 g (0.9M) of potassium tert-butoxide and 460 ml of anhydrous ethanol.

The mixture was poured onto ice and extracted with ether, whereupon the combined organic extracts were washed with brine until neutrality, dried over Na$_2$SO$_4$, filtered, concentrated and distilled.

There were thus obtained 111 g of a mixture having b.p. 62°–4°/5.32×10$^2$ Pa (yield 88%) consisting of 80% by weight of trans-2,2,3,6-tetramethyl-1-cyclohexanone and 20% of the corresponding cis isomer.

IR: 1710 cm$^{-1}$;

NMR (60 MHz): 0.8–1.15 (12H, 4s); 1.55–1.80 (4H, s); 1.8–2.2 (3H, m); 2.4–2.9 (6H, m) δppm;

MS: M$^+$=154(35); m/e: 136(1), 121(3), 112(17), 96(100), 84(46), 65(75), 55(35), 41(45), 27(50).

c. 1-(3-Hydroxy-1-hexynyl)-2,2,3,6-tetramethyl-1-cyclohexanol

495 Ml (1.16M) of a 15% solution of butyl-lithium in hexane were added under an atmosphere of nitrogen at −70°, and with vigorous stirring, to a mixture of 51 g (0.52M) of hexyn-3-ol in 250 ml of anhydrous tetrahydrofurane (THF).

The reaction mixture was then brought to room temperature and kept under stirring overnight.

After having been cooled again to −70°, there were added dropwise 0.3M of the mixture obtained under letter b. above in solution in 115 ml of THF and stirring was maintained for 3 hrs at −70°, then overnight at room temperature.

The reaction mixture was poured onto ice, extracted with ether, washed with brine until neutrality, dried over Na₂SO₄, filtered, concentrated and distilled. The desired product was obtained with yield of 65%.

IR: 3400 cm⁻¹;

NMR (60 MHz): 0.75–1.25(15H, m); 1.25–2.15(10H, m); 4.45(1H, t) δppm;

MS: M⁺=252; m/e: 234 (1), 219(12), 210(8), 191(46), 177(9), 163(16), 149(66), 135(35), 121(31), 111(38), 96(67), 83(36), 69(60), 55(91), 43(25), 41(92).

d. 1-(2,3,6,6-Tetramethyl-1-cyclohexylidene)-1-hexen-3-ol 0.22M of the diol obtained according to paragraph c. above in solution in 100 ml of THF were added dropwise to a suspension kept under nitrogen of 9.3 g (0.232M) of LiAlH₄ in 400 ml of THF.

The reaction mixture was kept refluxing for 4 hrs, whereupon it was stirred overnight at room temperature, then it was hydrolyzed with caution by successively adding thereto 9.3 ml of water, 9.3 ml of a 15% solution of NaOH and finally 27.9 ml of water. After filtration, the clear filtrate was concentrated under reduced pressure to give a residue which, upon distillation, gave the desired product having b.p. 63°–70°/13.3 Pa.

IR: 3350 and 1960 cm⁻¹;

NMR (60 MHz): 0.73–1.10(15H, m); 1.15–2.5(10H, m); 3.9–4.3 (1H, m); 5.35 (1H, 2×d) δppm;

MS: M⁺=236; m/e: 221(4), 203(5), 194(39), 175(18), 164(8), 149(54), 135(35), 121(84), 107(75), 95(55), 81(39), 71(65), 55(95), 43(100), 41(88).

EXAMPLE 2

Preparation of 1-(2-ethyl-2,6-dimethyl-1-cyclohexyl)-3-hexanol

15 G (63.6 mM) of 1-(2-ethyl-2,6-dimethyl-1-cyclohexylidene)-1-hexen-3-ol in 150 ml of acetic acid were hydrogenated at room temperature in the presence of 100 mg of PtO₂. After 6 hrs, 2.9 lt of hydrogen were absorbed. After filtration, the clear filtrate was concentrated, diluted with ether and successively washed with water, with a 10% solution of NaOH (2×), then with brine until neutrality. After drying, filtering and concentration, the filtrate was distilled to give 13.1 g of a fraction having b.p. 77°–93°/13.3 Pa.

A fractional distillation on a Vigreux column enabled the isolation of the desired product essentially consisting of the following isomers:

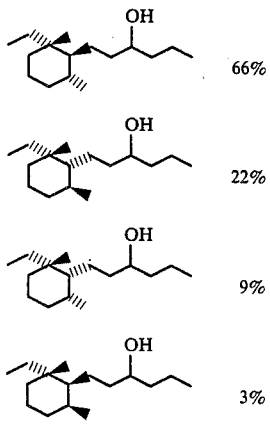

The analytical characteristics of the obtained isomeric mixture were the following:

IR: 3350 cm⁻¹;

NMR (360 MHz; CDCl₃): 0.59–0.65(1H, m); 0.73–0.97(12H, m); 1.0–1.65(17H, m); 1.82–1.96(1H, m); 3.5–3.61(1H, m) δppm;

MS: M⁺=240; m/e: 222(10), 221(20), 193(61), 179(1), 165(3), 152(22), 137(26), 123(97), 109(70), 95(68), 83(63), 69(61), 55(100), 41(57).

1-(2-Ethyl-2,6-dimethyl-1-cyclohexylidene)-1-hexen-3-ol, used as starting material in the process described above, can be prepared as follows:

a. 2-Ethyl-1-(3-hydroxy-1-hexynyl)-2,6-dimethyl-1-cyclohexanol 40.2 G (0.41M) of 1-hexyn-3-ol in 200 ml of anhydrous tetrahydrofurane (THF) have been placed in a three-necked reaction vessel and cooled to −70°. At this temperature there were added under stirring 390 ml (0.91M) of a 15% solution of butyl-lithium in hexane and the temperature was then raised to about 20° within one night. A solution of 40 g (0.26M) of 2-ethyl-2,6-dimethylcyclohexanone in 90 ml of THF-75/25 isomeric mixture of the following compounds

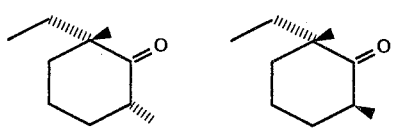

was added dropwise to the reaction mixture cooled again to −70°. After having been kept under stirring for 3 h at −70° and overnight at room temperature, the mixture was poured onto ice, extracted with ether, washed with brine until neutrality, dried over Na₂SO₄, filtered and concentrated.

On fractional distillation, there were obtained 27.3 g of a fraction of the desired product having b.p. 97°–127°/13.3 Pa.

IR: 3400 cm⁻¹;

NMR (60 MHz; CDCl₃): 0.65–1.18(12H); 1.2–1.85(13H, m); 4.46(1H, t, J=6) δppm;

MS: M⁺=252; m/e: 201(0), 184(5), 155(25), 141(33), 127(73), 109(19), 96(26), 85(97), 69(37), 55(100), 41(69).

b. 1-(2-Ethyl-2,6-dimethyl-1-cyclohexylidene)-1-hexen-3-ol

27 G (0.107M) of the diol obtained according to paragraph a. above in 70 ml of anhydrous THF were added dropwise under stirring and in a nitrogen atmosphere to a suspension of 4.28 g (0.107M) of LiAlH₄ in 200 ml of THF. The mixture was kept refluxing during 4 hrs, then overnight at room temperature. 4.28 Ml of water, 4.28 ml of a 15% NaOH solution and 12.84 ml of water were successively added with caution to the mixture and the whole was kept stirring for 1 h, whereupon the mixture was filtered, concentrated and fractionally distilled to give 16.9 g of the desired product having b.p. 62°–69°/13.3. Pa. This product was constituted by an isomeric mixture consisting of about 2.5:1 of the allenic carbinols of formula

and

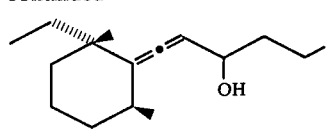

IR: 3375 and 1960 cm$^{-1}$;

NMR (60 MHz, CDCl$_3$): 0.60–1.15(12H), 1.2–2.1(13H, m); 3.95–4.3(1H, m); 5.2–5.45(1H, m) δppm;

MS: M$^+$=236; m/e: 219(1), 207(29), 194(14), 175(9), 165(11), 149(16), 135(100), 121(18), 107(39), 93(46), 81(33), 71(34), 55(73), 43(64), 41(51).

EXAMPLE 3

A base perfuming composition was prepared by mixing the following ingredients (parts by weight):

| IRALIA ®[1] | 120 |
| CYCLOSIA ® base[1] | 100 |
| EXALTOLIDE ®[1] 10%* | 100 |
| Musk ketone | 80 |
| Musk xylene | 70 |
| Musk ambrette | 60 |
| Coumarine | 60 |
| Trichloromethylphenyl-carbinyl acetate | 50 |
| Patchouli oil | 50 |
| Eugenol | 45 |
| Galbanum resinoid | 35 |
| Synth. white rose oil | 30 |
| LILIAL ® (L. Givaudan) | 30 |
| Vetyveryl acetate | 30 |
| Methyl eugenol | 20 |
| cis-10,10-Dimethyltricyclo[7.1.1.0$^{2,7}$]undec-2-en-4-one[1][2] | 20 |
| β-Ionone | 10 |
| Synth. jasmin oil | 10 |
| Benjoin resin of Siam | 10 |
| Deterpenated orange oil | 10 |
| | 940 |

*in dipropyl glycol
[1]origin: FIRMENICH SA, Geneva (Switzerland)
[2]see Swiss Patent No. 626,532

Three novel compositions were prepared by mixing the following ingredients (parts by weight):

| | A | B | C |
|---|---|---|---|
| Base composition | 94 | 94 | 94 |
| TIMBEROL[1] | — | 6 | — |
| Product of Example 1* | — | — | 6 |
| Anozol | 6 | — | — |
| | 100 | 100 | 100 |

*in solution at 5% in anozol
[1]origin: Dragoco, Holzminden, FRG

The compositions thus obtained were evaluated by a panel of perfumers who expressed the views that composition C was the best, the one which possessed the warmest, the deepest and the woodiest note.

Its odor strength was superior to that shown by the control composition A and by composition B obtained by using the prior art compound.

EXAMPLE 4

Two powder detergent bases were prepared by mixing the following ingredients (parts by weight):

| | Composition | Composition with sodium perborate |
|---|---|---|
| Sodium linear alkyl-benzenesulphonate (chain length: C$_{11-5}$) | 8.0 | 6.4 |
| Ethoxylated tallow alcohol (14EO) | 2.9 | 2.3 |
| Sodium soap (chain length: C$_{12-16}$ 13–26%; C$_{18-22}$ 74–87%) | 3.5 | 2.8 |
| Sodium triphosphate | 43.8 | 35.0 |
| Sodium silicate | 7.5 | 6.0 |
| Magnesium silicate | 1.9 | 1.5 |
| Carboxymethylcellulose | 1.2 | 1.0 |
| Sodium EDTA | 0.2 | 0.2 |
| Sodium sulphate | 21.2 | 17.0 |
| Water | 9.8 | 7.8 |
| Sodium perborate | — | 20.0 |
| | 100.0 | 100.0 |

By adding to a sample of each of the above detergent bases 1% of the product of Example 1, there were obtained two novel compositions having a powerful and elegant woody note.

EXAMPLE 5

By using the product of Example 1 at the concentration indicated, the following articles were perfumed:

| Lotion | 5.0% |
| Day cream | 0.4% |
| Night cream | 0.4% |
| Shampoos | 0.5% |
| Deodorant (aerosol) | 1.2% |
| Hair lacquer | 0.3% |
| Soap[1] | 0.5% |
| Talc | 0.5% |
| Chlorinated detergent powder | 0.2% |

[1]Type: LUX, Unilever

The addition of the product in question confers to the said articles a woody scent of good stability and strength.

Stability assays were effected on samples of each of the perfumed articles by storing them at 40° C. during 1 month. None of the samples examined showed any sign of coloration or odor modification.

What we claim is:

1. Cycloaliphatic alcohols of formula

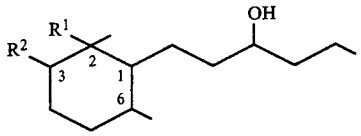

wherein each of symbols R$^1$ and R$^2$ designates a methyl radical or wherein R$^1$ designates an ethyl radical and R$^2$ stands for a methyl radical or a hydrogen atom.

2. 1-(2,2,3,6-Tetramethyl-1-cyclohexyl)-3-hexanol.
3. 1-(2-Ethyl-2,6-dimethyl-1-cyclohexyl)-3-hexanol.
4. 1-(2-Ethyl-2,3,6-trimethyl-1-cyclohexyl)-3-hexanol.
5. A compound according to claim 2 having formula

6. A compound according to claim 2 having formula

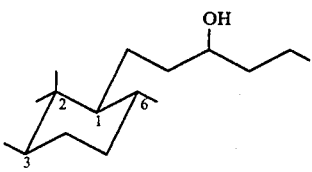

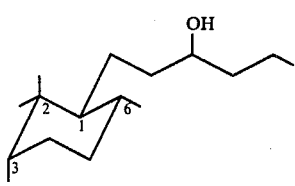

7. A perfume composition containing an odorous effective amount of a compound of formula (I) according to claim 1, together with perfumery coingredients, diluents or supports.

8. A process for modifying, improving or enhancing the odor properties of consumable articles which comprises the step of adding thereto an odorous effective amount of a compound according to claim 1.

9. The process of claim 8 wherein the consumable article is a solid or liquid detergent.

10. The process of claim 8 wherein the consumable article is a soap.

11. The process of claim 8 wherein the compound according to claim 1 is essentially in the trans isomeric form of formula

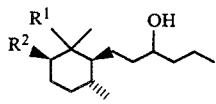 (a)

and

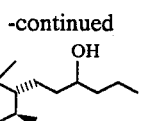 (d)

12. A process for the preparation of a compound according to claim 1, which comprises the step of reducing an allenic carbinol of formula

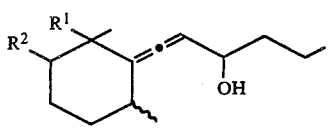 (II)

wherein ⁓⁓ stands for a single carbon-carbon bond of cis- or trans-configuration, said reduction being carried out by catalytic hydrogenation in homogeneous or heterogeneous phase at super-atmospheric pressure and in the presence of a noble metal catalyst.

13. The process according to claim 12 wherein the catalyst is palladium or palladium on charcoal.

14. A process for the preparation of a compound of formula (I) according to claim 1 essentially in the trans isomeric form of formula

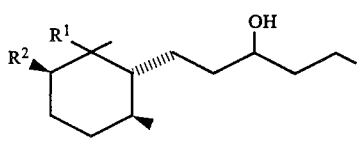

which comprises reducing a ketone of formula

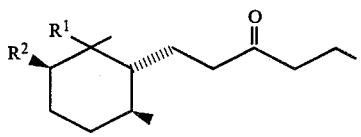 (III)

by means of an alkali metal alumino-hydride.

* * * * *